United States Patent [19]
Zenner et al.

[11] Patent Number: 6,007,494
[45] Date of Patent: Dec. 28, 1999

[54] DETERMINATION OF DATA CONCERNING A PERSON'S AUDITORY CAPACITY

[76] Inventors: Hans Peter Zenner, Burgholzweg 149, D-72070 Tuebingen; Anthony W. Gummer, Ahornweg 2, D-72138 Kirchentellinsfurt, both of Germany

[21] Appl. No.: 08/983,645

[22] PCT Filed: Jul. 24, 1996

[86] PCT No.: PCT/EP96/03258

§ 371 Date: Mar. 9, 1998

§ 102(e) Date: Mar. 9, 1998

[87] PCT Pub. No.: WO97/04706

PCT Pub. Date: Feb. 13, 1997

[30] Foreign Application Priority Data

Jul. 25, 1995 [DE] Germany .......................... 195 27 108

[51] Int. Cl.$^6$ .................................................. A61B 10/00
[52] U.S. Cl. ............................................................ 600/559
[58] Field of Search .................................. 600/559, 587; 73/585

[56] References Cited

U.S. PATENT DOCUMENTS

| | | | |
|---|---|---|---|
| 4,729,646 | 3/1988 | Clark et al. ............................... | 350/521 |
| 5,711,308 | 1/1998 | Singer ...................................... | 600/559 |
| 5,833,626 | 11/1998 | Leysieffer ............................... | 600/559 |

FOREIGN PATENT DOCUMENTS

| | | |
|---|---|---|
| 0 015 258 | 2/1979 | European Pat. Off. . |
| 0 084 972 | 8/1983 | European Pat. Off. . |
| 314 222 | 11/1970 | Germany . |
| 2 155 853 | 11/1971 | Germany . |
| 24 08 765 | 2/1974 | Germany . |
| 43 20 579 | 5/1993 | Germany . |
| 2 099 999 | 5/1982 | United Kingdom . |
| WO 89/01315 | 2/1989 | WIPO . |
| WO 93/21820 | 11/1993 | WIPO . |

OTHER PUBLICATIONS

Charles Koester et al, "Confocal slit divided–aperature microscope: applications in ear research" Applied Optics Feb. 1994.

Brochure of Polytec Optronics, Inc., Costa Mesa, CA, USA, 8 pages, "Fiber Optic Laser Vibrometer".

Applied Optics, Bd. 33, Nr. 4, Feb. 1, 1994, NY pp. 702–708, C.J. Koester et al. "Confocal slit divided–aperature microscope: applications in ear research".

HNO, Bd. 41, Nr. 1/93, Jan. 1993, DE, Seiten 1–6, N. Stache et al., "Laser–Doppler–Vibrometrie (LDV) des Trommelfells".

Journal of Biomechancial Engineering, Bd. 101, Nr. 4, Nov. 1979, New York (US), Seiten 267–270, J.M. Hamelink et al. "Ocular Tonometry Through Sonic Excitation and Laser Doppler Velocimetry".

Hearing Research, 51 (1991) 203–214, 1991 Elsevier Science Publishers B.V. 0378–5955/91, A. Nutall et al. "Laser Doppler velocimetry of basilar membrane vibration".

The American Journal of Otology, vol. 14, No. 3, May 1993, R. Goode et al. "Measurement of Umbo Vibration in human subjects—Method and possible clinical applications".

*Primary Examiner*—Max Hindenburg
*Attorney, Agent, or Firm*—Pennie & Edmonds LLP

[57] ABSTRACT

The invention concerns a device for determining data on auditory capacity, the device having preferably non-contact means for measuring vibrations of the middle-ear ossicles (22, 23, 24) and/or the tympanic membrane (21) by means of electromagnetic waves. The electromagnetic waves used for the measurement are input by means of a microscope (3), in particular an optical microscope (3). This microscope can be modular in design, and a module (5) can be provided for the input of a laser beam (9). The invention also concerns a method of determining data on auditory capacity, the method calling for the vibration of the middle ear and/or the eardrum to be measured by means of electromagnetic waves and, from the measurement signals thus obtained, the contributions to the total signal by the middle ear and/or the eardrum determined in at least one processing step.

22 Claims, 1 Drawing Sheet

DETERMINATION OF DATA CONCERNING A PERSON'S AUDITORY CAPACITY

BACKGROUND OF THE INVENTION

1. Field of the Invention

The invention relates to a device for sensing aural data.

2. Description of the Prior Art

Extensive investigation has already been done in obtaining qualitative, more particularly also quantitive, data relevant to the condition of normal and disturbed hearing, the discovery made by Kemp (see EP-B1.15258) being particularly of significance in this respect that sound emissions in the external canal can be measured as a reaction to a sound event which are indicative of the condition in the ear. These so-called evoked otoacoustic emissions were measured by Kemp with the aid of an acoustic sensor comprising a highly-sensitive miniature microphone and a sound emitter. It is also known that otoacoustic emissions may also materialize spontaneously, i.e. without the ear being stimulated from without.

Direct ear-drum vibration measurement in examining the mechanics of the middle ear is already being done by the method of laser Doppler vibrometry. This method is described in the German publication of N. Stasche, H. -J. Foth and K. Hormann in HNO (1993), 41, pages 1 to 6. In this method the beam of a He—Ne laser is split by a beam divider and the two component beams, one of which is directed at the object being examined, are subsequently caused to produce an interference effect. From the shift in frequency the amplitude of the sensed point in the ear-drum is determined. For inputting the laser light to the object being examined Stasche et al make use of a flexible fiber optic lightguide which needs to be located in the immediate vicinity of this object. Apart from problems as to resolution (small aperture) this may also make measuring difficult on the patient since the fiber optic lightguide must not come into contact with the ear-drum.

SUMMARY OF THE INVENTION

The object of the invention is to further improve aural sensing, more particularly by obtaining data permitting quantification, in obviating the drawbacks of prior art as described. More particularly, the object is to provide a device making it possible to simply obtain measurement data without stressing the patient substantially. It is a further object to make the device and a corresponding method suitable for obtaining information—where necessary, following analysis—as to the condition of the middle and/or internal ear capable of assisting the physician as a basis for diagnosis and/or therapy.

This object is achieved by a device as set forth in claim 1. Preferred embodiments of the device read from the dependent claims 2 to 16, whereby the wording of all claims is made with reference to the contents of the description.

The device in accordance with the invention for sensing aural data comprises means for, more particularly, non-contact vibration measurement of the middle ear and/or ear-drum with the aid of electromagnetic waves, whereby for inputting the electromagnetic waves used to the object being sensed a microscope, more particularly an optical microscope, is provided.

Inputting is done such that the electromagnetic beams are, more particularly, guided through the optical system of the microscope onto the object being sensed. The beams reflected from the object being sensed are preferably returned likewise through the optical system of the microscope and subsequently analyzed. Compared to known devices as described, accuracy is enhanced by this measurement arrangement, as a result of which events taking place in the ear can be detected and quantified which formerly thwarted measurement. This is due, among other things, to the device in accordance with the invention enabling the majority of the reflected electromagnetic waves to be guided into the analyzer (high aperture) correspondingly improving the signal-to-noise ratio.

As described, the device in accordance with the invention is designed to measure the vibration of the middle ear and/or ear-drum, thus making it primarily possible to measure vibrations in the ear-drum and fundamentally in all ossicles. In this arrangement sensing the measurement data is typically done on the ear-drum in an outpatient operation since sensing hearing in this case does not require any surgery.

The microscope concerned is expediently a so-called otomicroscope, i.e. an instrument in standard use in this field. Both in these cases and in general a modified operation microscope may be put to use in the device in accordance with the invention.

The microscope is configured preferably modular, i.e. comprising several components which can be composed dedicated to the particular application concerned. In accordance with the invention one such modular microscope comprises an interchangeable module for electromagnetic wave inputting, as a result of which the microscope can be put to use both for the invention and for other applications.

In one aspect of the invention the microscope comprises at least one mirror for electromagnetic wave inputting, more particularly a deflection mirror. In the preferred embodiments as described this mirror is provided in the interchangeable module, the mirror serving to direct the electromagnetic waves beamed into the microscope through the (optical) system onto the object being sensed, where necessary including a deflection. Correspondingly, the mirror may serve to redirect the reflected beams from the microscope.

It is to be noted in this context that the invention also relates to a module, more particularly a interchangeable module including the aforementioned features. One such module is configured so that it can be inserted in or mounted on a corresponding usual-type microscope, as a result of which such a microscope is suitable for use in the invention.

In the device in accordance with the invention vibration measurement is done preferably with the aid of coherent electromagnetic radiation to simplify measuring and analysis. More particularly, laser radiation is provided for the measurement, for example, as produced by a helium-neon laser. Such a laser operates, for example, on a wavelength of 633 nm.

The means for measuring vibration comprise more particularly an interferometer, i.e. an instrument with the aid of which interference phenomena can be determined between the electromagnetic waves irradiated and reflected, one such interferometer being preferably a typically so-called vibrometer, the configuration and function of which is known to the person skilled in the art. In laser measurement known laser vibrometers, more particularly the so-called laser Doppler vibrometers, can be put to use as described, for example, in the publication of Stasche et al. as cited above. Accordingly the contents of this publication are made a component of the present description.

As already indicated, the device in accordance with the invention can be provided for detecting events occurring spontaneously in the ear, more particularly in the internal ear, with the aid of vibration measurement. To obtain results which bear comparison and are reproducible the events may also be be evoked, i.e. prompted by an (external) influence. In these cases the device in accordance with the invention comprises stimulation means with the aid of which the events in the ear, more particularly in the internal ear, can be prompted, for example, by stimulating it from without.

The cited stimulation means may be situated as near as possible to the ear-drum and/or the ossicles of the middle ear to prompt stimulation as efficiently as possible. In this arrangement suitable means of transfer may be provided which introduce the "stimulation" to the correspondingly portion of the middle ear or ear-drum, such means being, for example, cannulae, wires or means having a similar effect. To prevent injury of the object being sensed, the stimulation means or transfer means should not be allowed to come in contact with the object being sensed, where possible. For this purpose suitable locating means may be provided to maintain the transfer means spaced away from the object being sensed, this applying at least then, when sensing is done on a living object. Where this is not the case, it may be preferred to arrange for the stimulation means or transfer means to be in direct contact with the ear-drum or ossicles to achieve improved transfer of stimulation.

In preferred embodiments the stimulation means are designed for an acoustic stimulation, such stimulation means comprising more particularly a source of sound preferably arrangable in the external canal or in connection with the external canal. This acoustic stimulation may be, for example, a "noise", i.e. a superposition of an "infinte" number of tones. To provide defined acoustic stimuli, more particularly, two sinusoidal tones having the frequencies $f_1$ and $f_2$ may also be made use of simultaneously, as a result of which emissions are evoked in the internal ear, more particularly the so-called $2f_1-f_2$ and higher distortion products which are then detected in the ear-drum or ossicles by vibration measurement. In a modification thereof more than two sinusoidal tones or sinewave signals, i.e. a so-called multi-sinewave signals may also be employed for stimulation.

In other preferred embodiments the stimulation means is designed to mechanically stimulate the middle ear. In this case, more particularly, a so-called piezoelectric transducer may be provided, whereby the supply wire of this transducer may be additionally guided in a cannula to the piezo-element. Where necessary, one such stimulation means may be directly fitted to an ossicle, more particularly to the so-called stirrup.

In other preferred embodiments the stimulation means is designed for (direct) electrical stimulation, more particularly, an electrode being provided which may be, for example, directly guided to the cochlea in the internal ear.

In another aspect of the invention the device in accordance with the invention comprises means for analyzing the signals obtained from measuring vibration of the middle ear and/or ear-drum. In addition to such means of analysis corresponding detectors are, of course, provided for detecting the electromagnetic radiation, more particularly laser detectors and means for decoding spectral data, more particularly so-called laser decoders for decoding the signals sensed.

The cited means of analysis comprise preferably a so-called analyzer, more particularly a software analyzer with the aid of which the components contributed by the middle ear and/or the internal ear can be derived from the signal as received and, where necessary, decoded. The signal obtained from sensing consists substantially of three components, namely the input signal with which the sensed object is irradiated, the "middle ear component" and the "internal ear component". This is the reason why the analyzer, more particularly the software analyzer, needs to be able to respond to the component represented by the input signal and, where necessary, to derive from the remaining "vestigial signal" the components contributable to the middle ear or the internal ear. This can be achieved more particularly by means of a suitable software reflecting the model conceptions or values gained from experience in experiment relevant to the components to be eliminated individually.

The invention relates also to a microscope, more particularly, to an optical microscope designed to input electromagnetic waves for preferably non-contact vibration measurement of the ossicles of the middle ear and/or ear-drum, express reference being made in this context to the corresponding passages of the present description disclosing further features of this microscope.

Part and parcel of the invention is furthermore using the device described in accordance with the invention or microscope in accordance with the invention for detecting events occurring in the internal ear, this use making it possible for the first time to detect such events or derive data obtained thereby. Preferably involved are events taking place in the internal ear, the so-called micromechanic events, this term covering substantially all events contributable to the generation of mechanical energy in the internal ear. It is in this context that also so-called otoacoustic emissions (OAE) are involved which, as already mentioned, may occur or be evoked spontaneously. Since these can be inhibited or suppressed by pharmaceuticals, precisely investigating these effects is of special significance.

In conclusion the invention relates to a method of sensing aural data making use more particularly of a device as described in accordance with the invention. In one such method vibrations of the middle ear (its ossicles) and/or ear-drum are measured preferably in non-contact measurement with the aid of electromagnetic waves. From the signals obtained, which as mentioned are composed substantially of a component of the input signal of the electromagnetic wave irradiation, a component of the middle ear and a component of the internal ear, the components contributed by the middle ear and/or internal ear relative to the signal as a whole are established in at least one step in analysis. In this method it is preferably the component contributed by the internal ear that is established, i.e. defining for the first time the component contributable to events in the internal ear relative to the signal detected as a whole.

Sensing the individual components can be done in various ways. For certain applications it may be sufficient when merely the component of the input signal is deducted from the signal as a whole. In such cases useful data may already be obtained from the remaining component (middle ear and internal ear) from which an internal ear component may also be derived in some circumstances. Preferably both the input signal component and a component contributable to the middle ear is deducted from the signal as a whole, the term "deducting" in this case being understood in the context of the usual Fourier transformation of the data sensed wherein the spectral data are decoded by ways and means known to the person skilled in the art. It will, of course, be appreciated that the individually components can be separated from each other by known equivalent methods.

The method in accordance with the invention can be implemented as mentioned by employing the device in accordance with the invention in, more particularly, making use of an optical microscope for inputting electromagnetic waves.

For vibration measurement the method in accordance with the invention preferably irradiates the ear-drum and/or at least one ossicle with a single beam of the electromagnetic waves, more particularly a laser beam.

In a further aspect characterizing the method laser light is beamed onto the ear-drum through an optical microscope, the reflected laser beam caused to interfere with the input laser beam, the sensed data decoded in the usual way and subsequently the middle ear and/or internal ear components of the signal obtained as a whole detected. The laser used for this purpose is, more particularly, a helium-neon laser. The reflected laser beam is likewise preferably directed through the optical microscope and subsequently caused to interfere with the input laser beam. When employing a laser vibrometer, beam splitting is done in the vibrometer and interference of the individual beams is undertaken in the detector part of the vibrometer.

Here too, the method is designed for deducting the input signal component from the signal obtained as a whole and deriving characteristics of the internal ear from the final signal thus obtained, where necessary, by deducting the signal components contributable to the middle ear. For deducting the middle ear component, data stemming from at least one (mathematical) model and/or gained from experience, e.g. in clinical tests, can be made use of which reflect or represent, more particularly, movement of the ossicles in the audible range.

As already mentioned, in the method described at least the (overall) component of the signal sensed contributable to the middle ear and the internal ear is detected which may already contain valuable information. In addition, where necessary, the contribution made exclusively by the internal ear can be obtained from this "vestigial signal" by deducting the middle ear component. This is important, on the one hand, in primarily examining functioning of the ear and, on the other, it is a requirement in effectively treating diseases associated with dysfunctions of the internal ear, such as Menière's disease, for example.

It is especially significant in this respect that the invention makes it possible, among other things, to gain information as to the internal ear from sensing the ear-drum, the latter being possible namely relatively simply, for instance, in the polyclinic.

The features as described and further to the invention read from the following description of preferred embodiments in conjunction with the sub-claims and the drawings, whereby each of the individual features may be achieved individually or in combination with each other.

BRIEF DESCRIPTION OF THE DRAWINGS

The following is a brief description of the drawings in which.

DETAILED DESCRIPTION

Figure 1:
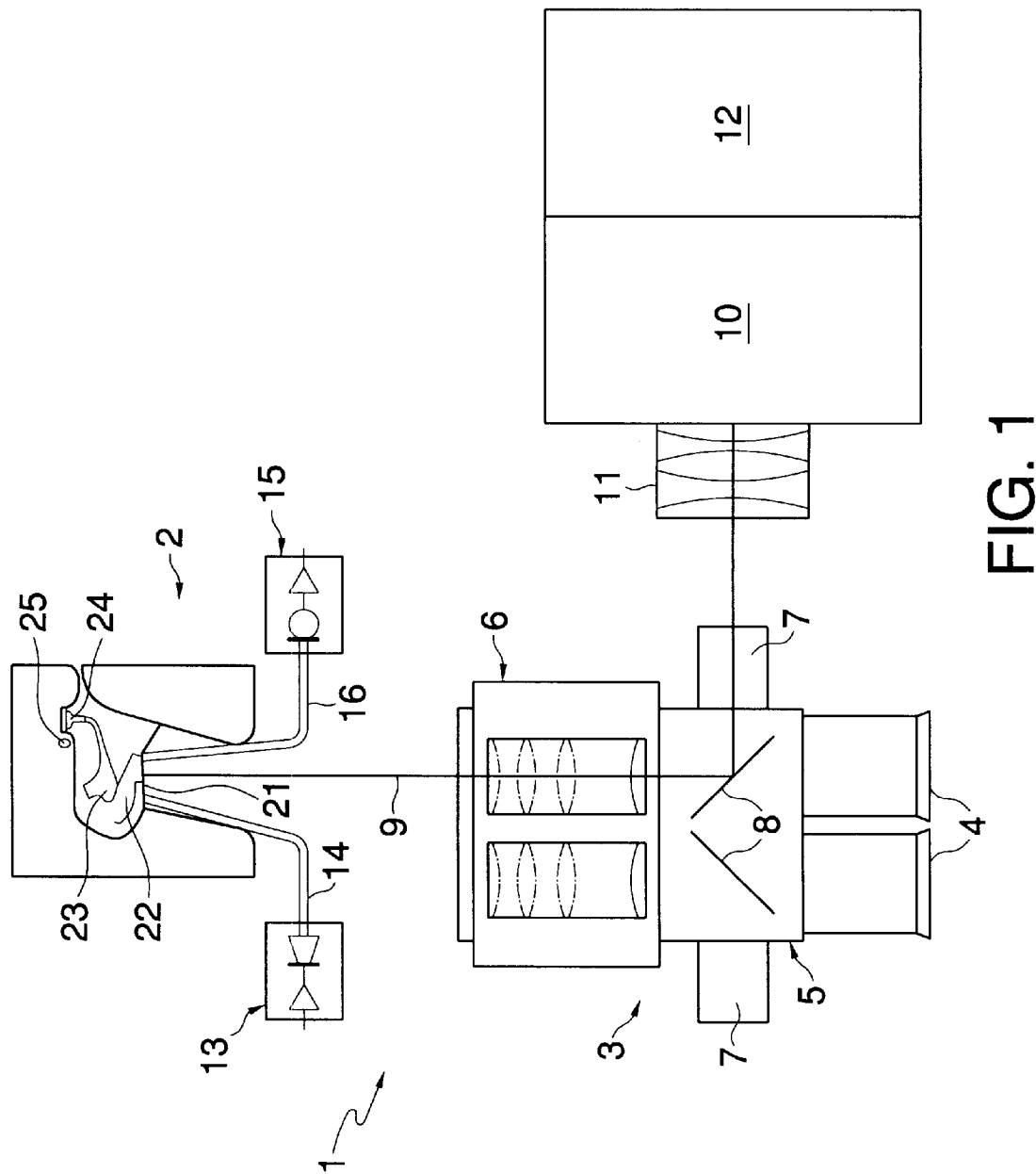
FIG. 1 is a schematic illustration of a device in accordance with the invention for implementing aural measurement on a sensed object.

Referring now to FIG. 1 there is illustrated a device 1 in accordance with the invention provided for detecting the data of a sensed object 2.

The device 1 comprises an optical microscope 3 configured substantially by a binocular 4, a module 5 for inputting laser beams and an operation microscope head 6. The module 5 includes two input means 7 each assigned deflection mirrors 8 with the aid of which a laser beam can be input into the microscope 3. In the case illustrated a laser beam 9 is input via the right-hand interchangeable module 7 and the right-hand deflection mirror 8 through the right-hand optics (not identified) of the head 6 and directed onto the object being sensed 2, the laser beam being able to be directed at the desired location on the object 2 by the binocular 4.

Furthermore evident schematically from FIG. 1 is a laser Doppler vibrometer 10 assigned to the right-hand interchangeable module 7 on the module 5 via a focussing objective 11. The laser Doppler vibrometer (LDV) is made up the actual vibrometer and a laser detector, both of which are not identified. The LDV 10 is typical in design, an analyzer unit 12 being connected thereto and likewise shown merely schematically in FIG. 1. This analyzer unit 12 is configured substantially as an analyzer for the spectrum obtained from the LDV 10 for decoding the data sensed, and a software analyzer.

The laser Doppler vibrometer 10 illustrated in FIG. 1 is intended for use of a He—Ne laser having a wavelength of 633 nm. A component or a detector part can be connected to the analyzer unit 12 for controlling the device or further processing or imaging the data sensed.

FIG. 1 shows furthermore below the object being sensed 2 a source of sound 13 as an otoacoustic means of evoking stimulation. The source 13 is connected to the object being sensed 2 by a transfer means 14, for example, in the form of a cannula. In addition, the object being sensed 2 is assigned a (probe) microscope 15 via a corresponding transfer means 16 with which the sound pressure generated by the source of sound 13 is measured. It is this value to which the value measured by the vibrometer is related, for example μm/s, relative to Pascal. If evocation is done with the aid of an electrode the vibration value obtained would be related correspondingly to Ampere. The amplifiers of the corresponding signals identified neither in the illustration of the source of sound 12 nor in that of the probe microphone 15 are indicated in the drawing. For holding in place the transfer means 14, 16, e.g. the cannulae, locating means for example in the form of a conical retaining elements may be provided preventing contact of the transfer means 14, 16 with the object being sensed 2, i.e. maintaining them, where necessary, at a defined spacing away from the object 2.

The object being sensed 2 is illustrated in FIG. 1 to schematically represent the human ear. The laser beam 9 is directed at the ear-drum 21 adjoined by the hammer 22, ambos 23 and stirrup 24. In conclusion the fenestra vestibuli 25 is indicated.

The method in accordance with the invention as described above is likewise evident from reference to FIG. 1. The laser beam 9 emitted by the laser Doppler vibrometer 10 is fed after focussing by the microscope 3 to the object being sensed 2. The reflected laser beam 9 is returned in the same way through the microscope 3 and caused to interfere with a corresponding partial beam in the LDV 10 (in the detector part thereof).

The spectral data sensed are decoded and analyzed as described by the software analyzer and imaged by further devices. Controlling the system is done by a computer, more particularly a trigger signal being transferred on evocation by the source of sound 13.

What is claimed is:

1. A method of sensing data relevant to events occurring in an internal ear, said method comprising inputting coherent electromagnetic waves from an interferometer, via a focusing objective associated therewith and directly arranged thereon, directly into an optical microscope, beaming said waves through said optical microscope onto at least one of an ossicle of the middle ear and the ear-drum, wherein reflected waves interfere with said input waves, and determining from a resulting measured signal an internal ear component thereof by deducting a middle ear component, said middle ear component being determined from at least one of model data and data gained from experience and representing movement of the ossicles in the audible range.

2. The method as set forth in claim 1, wherein said coherent electromagnetic waves are comprised of laser radiation.

3. The method as set forth in claim 2, which further comprises choosing a helium-neon laser as said laser.

4. A device for sensing data relevant to events occurring in an internal ear by non-contact vibration measurement of ossicles in at least one of a middle ear portion and an ear-drum with coherent electromagnetic waves, said device comprising an optical microscope, an interferometer and analysis means for analyzing signals or data obtained by use of said device, wherein electromagnetic waves from said interferometer are input directly into said microscope via a focusing objective associated with said interferometer, arranged directly by said microscope, aimed at at least one of the ossicles and ear-drum and are guidable by said microscope after reflection back into said interferometer.

5. The device as set forth in claim 4, wherein said microscope is a surgical microscope.

6. The device as set forth in claim 4, wherein said microscope comprises at least one mirror.

7. The device as set forth in claim 4, wherein said interferometer comprises a vibrometer.

8. The device as set forth in claim 4, which further comprises means for stimulation of the ear assignable to or arrangeable in an external ear canal by which events can be stimulated in the ear, said stimulation means being introduced as near as possible to at least one of the ear-drum and the ossicles without coming into contact therewith.

9. The device as set forth in claim 8, wherein said stimulation means provides acoustic stimulation.

10. The device as set forth in claim 4, wherein said analysis means comprises a software analyzer capable of deriving components of the inner ear which contribute toward the measured signals.

11. The device as set forth in claim 6, wherein said at least one mirror is a deflection mirror.

12. The device as set forth in claim 7, wherein said interometer is a laser Doppler vibrometer.

13. The device as set forth in claim 9, wherein said stimulation means is arranged in an external ear canal.

14. A method of sensing aural data with a device comprising means for producing electromagnetic waves; means for measuring vibrations of at least one of a middle ear portion and an eardrum of an ear caused by said electromagnetic waves; and a microscope which permits passage of said waves into said ear, which method comprises transmitting electromagnetic waves into an inner portion of the ear, measuring vibrations of at least one of the middle ear and the eardrum due to said electromagnetic waves, converting said measured vibrations into a signal composed of an input signal component, a middle ear component and an internal ear component, and determining from said signal at least one of the middle ear and internal ear components.

15. The method of claim 14, which comprises determining the internal ear signal component.

16. The method of claim 14, wherein the internal ear signal component is determined by deducting from the total signal the input signal component and the middle ear signal component.

17. The method of claim 14, wherein said electromagnetic waves are configured into a single beam.

18. The method of claim 17, wherein said single beam is a laser beam.

19. The method of claim 14, wherein said electromagnetic waves are transmitted in the form of a laser beam inputted through said microscope onto the ear-drum, a reflected portion of said laser beam is caused to interfere with the input laser beam, a total signal is generated representing data produced thereby and at least one of a middle ear component and an inner ear component of said signal is deduced from the total signal.

20. The method of claim 19, which further comprises deducting a laser light input signal component from said total signal and determining characteristics of the inner ear portion from a remaining signal portion.

21. The method of claim 19, which further comprises deducting a laser light input signal component and a middle ear signal component from said total signal.

22. The method of claim 21, wherein said middle ear signal component is deducted based upon data from at least one of a model and from previous experience, said data comprising a record of movement of the ossicles in the audible range of the electromagnetic spectrum.

* * * * *